US012682441B2

(12) United States Patent      (10) Patent No.:    US 12,682,441 B2

Sah et al.        (45) Date of Patent:      Jul. 14, 2026

---

(54) IMPLEMENTING IMAGE ENHANCEMENT FOR IMPROVED DEFECT DETECTION

(71) Applicant: KLA Corporation, Milpitas, CA (US)

(72) Inventors: Kaushik Sah, Kessel Lo (BE);
Thirupurasundari Jayaraman,
Chennai (IN); Srikanth Kandukuri,
Hyderabad (IN); Andrew James Cross,
Cheshire (GB); **Gangadharan
Sivaraman**, Chennai (IN)

(73) Assignee: KLA Corporation, Milpitas, CA (US)

( * ) Notice: Subject to any disclaimer, the term of this patent is extended or adjusted under 35 U.S.C. 154(b) by 735 days.

(21) Appl. No.: 17/673,370

(22) Filed: Feb. 16, 2022

(65) Prior Publication Data

US 2022/0270212 A1     Aug. 25, 2022

Related U.S. Application Data

(60) Provisional application No. 63/153,380, filed on Feb. 25, 2021.

(51) Int. Cl.
| | |
|---|---|
| *G06T 7/00* | (2017.01) |
| *G06T 5/60* | (2024.01) |
| *G16H 10/40* | (2018.01) |
| *G16H 30/40* | (2018.01) |

(52) U.S. Cl.
CPC .............. *G06T 7/0004* (2013.01); *G06T 5/60* (2024.01); *G16H 10/40* (2018.01); *G16H 30/40* (2018.01); *G06T 2207/20081* (2013.01)

(58) Field of Classification Search
CPC . G06T 2207/20081; G06T 2207/20084; G06T 2207/30148; G06T 7/00; G06T 3/4046
See application file for complete search history.

(56) References Cited

U.S. PATENT DOCUMENTS

| | | | |
|---|---|---|---|
| 7,826,047 | B2 | 11/2010 | Shibata et al. |
| 9,875,536 | B2 | 1/2018 | Konecky |
| 9,996,942 | B2 | 6/2018 | Bhattacharyya et al. |

(Continued)

FOREIGN PATENT DOCUMENTS

| | | |
|---|---|---|
| KR | 1020170129892 A | 11/2017 |
| KR | 1020180095708 A | 8/2018 |

(Continued)

OTHER PUBLICATIONS

Ge et al., Deep learning analysis on microscopic imaging in materials science, Materials Today Nano, vol. 11, Aug. 2020, 100087, pp. 1-20, doi.org/10.1016/j.mtnano.2020.100087.*

(Continued)

*Primary Examiner* — Guillermo M Rivera-Martinez

(74) *Attorney, Agent, or Firm* — Suiter Swantz IP

(57) ABSTRACT

A system and method for enhancing image quality. The system and method acquire a machine learning model trained for correlating one or more training images and one or more training design images. The system and method receive one or more sample specimen images corresponding to one or more features of a sample specimen. The system and method enhance the one or more sample specimen images by generating one or more enhanced images with the machine learning model based on at least the one or more sample specimen images.

45 Claims, 7 Drawing Sheets

500 —

502 — ACQUIRE, WITH A CHARACTERIZATION SUB-SYSTEM, ONE OR MORE TRAINING IMAGES COMPRISING ONE OR MORE TRAINING FEATURES OF ONE OR MORE TRAINING SPECIMENS

504 — RECEIVE THE ONE OR MORE TRAINING DESIGN IMAGES CORRESPONDING TO THE ONE OR MORE TRAINING FEATURES OF THE ONE OR MORE TRAINING SPECIMENS

506 — ALIGN THE ONE OR MORE TRAINING IMAGES WITH ONE OR MORE TRAINING DESIGN IMAGES CORRESPONDING TO THE ONE OR MORE TRAINING FEATURES OF THE ONE OR MORE TRAINING SPECIMENS

508 — GENERATE A MACHINE LEARNING MODEL BASED ON THE ONE OR MORE TRAINING IMAGES AND THE ONE OR MORE TRAINING DESIGN IMAGES

510 — RECEIVE ONE OR MORE SAMPLE SPECIMEN IMAGES CORRESPONDING TO ONE OR MORE FEATURES OF A SAMPLE SPECIMEN

512 — ENHANCE THE ONE OR MORE SAMPLE SPECIMEN IMAGES BY GENERATING ONE OR MORE ENHANCED IMAGES WITH THE MACHINE LEARNING MODEL BASED ON AT LEAST THE ONE OR MORE SAMPLE SPECIMEN IMAGES

514 — DETERMINE ONE OR MORE CHARACTERISTICS OF THE SPECIMEN BASED ON THE ONE OR MORE ENHANCED IMAGES

(56) References Cited

U.S. PATENT DOCUMENTS

| | | | |
|---|---|---|---|
| 10,043,261 B2 | 8/2018 | Bhaskar et al. | |
| 10,146,036 B2 | 12/2018 | Dhagat et al. | |
| 10,181,185 B2 | 1/2019 | Park et al. | |
| 10,211,025 B2 | 2/2019 | Lee et al. | |
| 10,346,740 B2 | 7/2019 | Zhang et al. | |
| 10,365,639 B2 | 7/2019 | Ghadar et al. | |
| 10,395,362 B2 | 8/2019 | Gupta et al. | |
| 10,416,087 B2 | 9/2019 | Zhang et al. | |
| 10,607,119 B2 | 3/2020 | He et al. | |
| 10,733,744 B2 | 8/2020 | Ha et al. | |
| 10,789,695 B2 | 9/2020 | Putman et al. | |
| 10,832,092 B2 | 11/2020 | Shaubi et al. | |
| 10,846,845 B2 | 11/2020 | Machek et al. | |
| 10,867,108 B2 | 12/2020 | Chao | |
| 10,949,964 B2 | 3/2021 | Pandey et al. | |
| 11,119,060 B2 | 9/2021 | Saraswatula et al. | |
| 11,170,255 B2 | 11/2021 | Riley et al. | |
| 11,177,111 B2 | 11/2021 | Ito et al. | |
| 11,379,967 B2 | 7/2022 | George et al. | |
| 11,468,553 B2 | 10/2022 | Kulkarni et al. | |
| 11,551,348 B2 | 1/2023 | Zhang et al. | |
| 11,580,398 B2 | 2/2023 | Zhang et al. | |
| 11,880,193 B2 | 1/2024 | Yati et al. | |
| 12,189,307 B2 | 1/2025 | Wang et al. | |
| 2007/0121106 A1* | 5/2007 | Shibata | G01N 21/8806 |
| | | | 356/237.2 |
| 2016/0275672 A1 | 9/2016 | Bhattacharyya et al. | |
| 2016/0292840 A1* | 10/2016 | Konecky | G06T 7/001 |
| 2017/0047195 A1* | 2/2017 | Lee | H01L 22/12 |
| 2017/0191945 A1* | 7/2017 | Zhang | G06T 7/001 |
| 2017/0192411 A1* | 7/2017 | Ghadar | G06N 20/00 |
| 2017/0200264 A1* | 7/2017 | Park | G06T 7/001 |
| 2017/0200265 A1* | 7/2017 | Bhaskar | G06T 7/0004 |
| 2017/0351952 A1* | 12/2017 | Zhang | G06V 10/764 |
| 2017/0352145 A1 | 12/2017 | Dhagat et al. | |
| 2018/0107928 A1* | 4/2018 | Zhang | G06N 3/082 |
| 2018/0293721 A1* | 10/2018 | Gupta | G06N 3/045 |
| 2018/0330511 A1* | 11/2018 | Ha | G06F 30/00 |
| 2019/0072505 A1 | 3/2019 | Saraswatula et al. | |
| 2019/0073568 A1* | 3/2019 | He | G06F 18/40 |
| 2019/0294923 A1 | 9/2019 | Riley et al. | |
| 2020/0013155 A1* | 1/2020 | Putman | G06T 3/4038 |
| 2020/0034956 A1* | 1/2020 | Machek | G06T 7/001 |
| 2020/0089130 A1* | 3/2020 | Chao | G06F 30/398 |
| 2020/0098101 A1* | 3/2020 | Pandey | G06T 3/4053 |
| 2020/0143528 A1* | 5/2020 | Kulkarni | G06V 20/69 |
| 2020/0226420 A1* | 7/2020 | Shaubi | G06V 10/993 |
| 2020/0234428 A1* | 7/2020 | George | G06N 3/082 |
| 2020/0327654 A1* | 10/2020 | Zhang | G06T 7/0004 |
| 2020/0335300 A1* | 10/2020 | Ito | H01J 37/222 |
| 2021/0026338 A1* | 1/2021 | Yati | G06T 7/0006 |
| 2021/0241449 A1* | 8/2021 | Wang | G03F 7/7065 |

FOREIGN PATENT DOCUMENTS

| | | |
|---|---|---|
| TW | 202105264 A | 2/2021 |
| WO | 2019046141 A1 | 3/2019 |

OTHER PUBLICATIONS

International Search Report and Written Opinion in PCT/US2022/017592 dated Jun. 13, 2022, 8 pages.

Chinese Patent Office, Office Action received in CN Application No. 202280012981.4, Jun. 23, 2025, 24 pages (including translation).

Korean Intellectual Property Office, Office Action received in KR Application No. 10-2023-7029987, Sep. 12, 2025, 16 pages (including translation).

Taiwan Patent Office, Office Action received in TW Application No. 111107158, Sep. 17, 2025, 16 pages (including translation).

* cited by examiner

TRAINING A MACHINE LEARNING MODEL

300

234

TRAINING IMAGES

302

TRAINING DESIGN IMAGES

304

MACHINE LEARNING MODEL

FIG. 3A

TRAINED MACHINE LEARNING MODEL

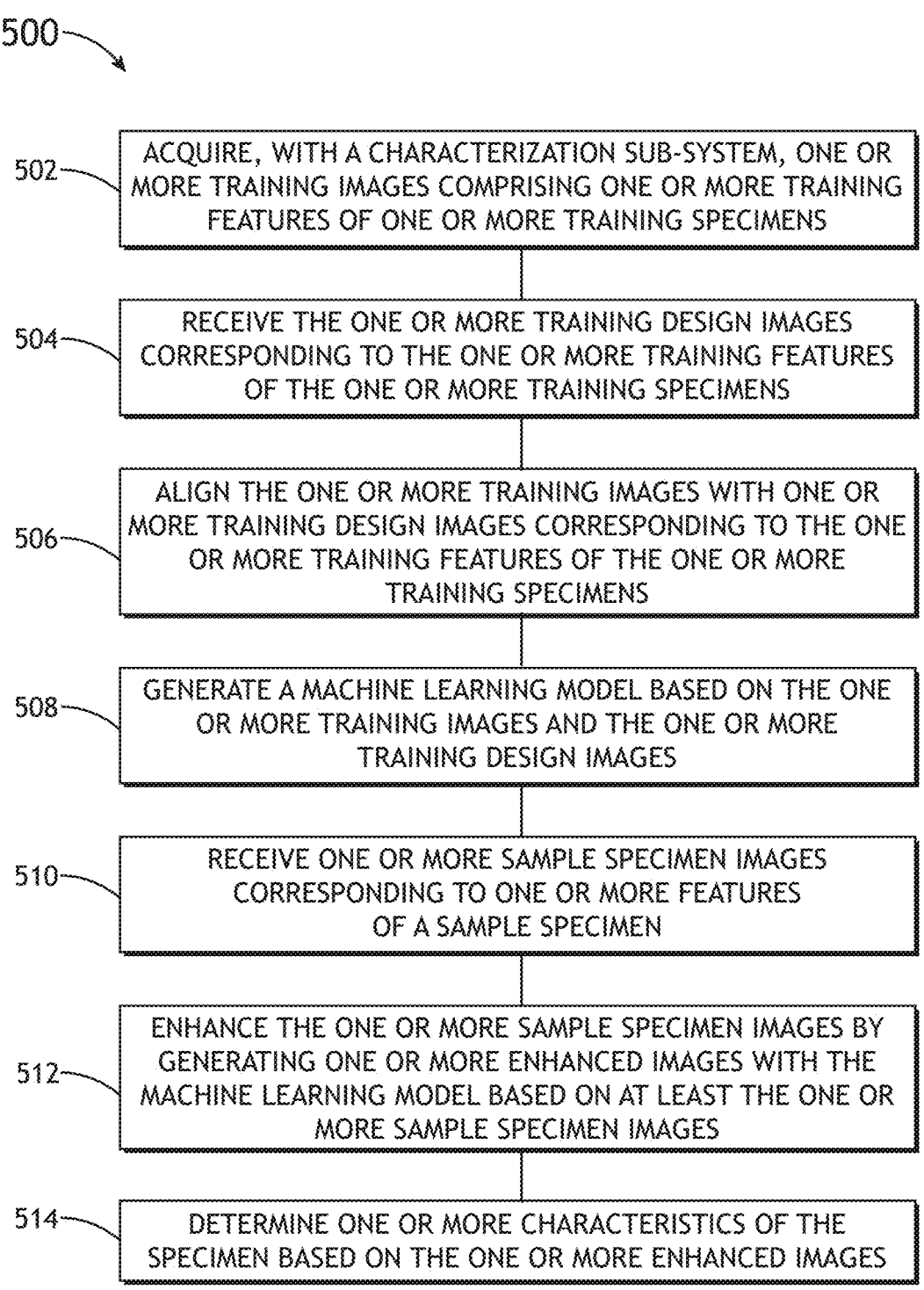

500

502 — ACQUIRE, WITH A CHARACTERIZATION SUB-SYSTEM, ONE OR MORE TRAINING IMAGES COMPRISING ONE OR MORE TRAINING FEATURES OF ONE OR MORE TRAINING SPECIMENS

504 — RECEIVE THE ONE OR MORE TRAINING DESIGN IMAGES CORRESPONDING TO THE ONE OR MORE TRAINING FEATURES OF THE ONE OR MORE TRAINING SPECIMENS

506 — ALIGN THE ONE OR MORE TRAINING IMAGES WITH ONE OR MORE TRAINING DESIGN IMAGES CORRESPONDING TO THE ONE OR MORE TRAINING FEATURES OF THE ONE OR MORE TRAINING SPECIMENS

508 — GENERATE A MACHINE LEARNING MODEL BASED ON THE ONE OR MORE TRAINING IMAGES AND THE ONE OR MORE TRAINING DESIGN IMAGES

510 — RECEIVE ONE OR MORE SAMPLE SPECIMEN IMAGES CORRESPONDING TO ONE OR MORE FEATURES OF A SAMPLE SPECIMEN

512 — ENHANCE THE ONE OR MORE SAMPLE SPECIMEN IMAGES BY GENERATING ONE OR MORE ENHANCED IMAGES WITH THE MACHINE LEARNING MODEL BASED ON AT LEAST THE ONE OR MORE SAMPLE SPECIMEN IMAGES

514 — DETERMINE ONE OR MORE CHARACTERISTICS OF THE SPECIMEN BASED ON THE ONE OR MORE ENHANCED IMAGES

FIG.5

IMPLEMENTING IMAGE ENHANCEMENT FOR IMPROVED DEFECT DETECTION

CROSS-REFERENCE TO RELATED APPLICATION

The present application claims the benefit under 35 U.S.C. § 119(e) of U.S. Provisional Application Ser. No. 63/153,380, filed Feb. 25, 2021, entitled Methods for Improving Optical Inspection and Metrology Image Quality Using Chip Design Data, naming Kaushik Sah, Thiru-purasundari Jayaraman, Srikanth Kandukuri, Andrew James Cross, and Gangadharan Sivaraman as inventors, which is incorporated herein by reference in the entirety.

TECHNICAL FIELD

The present invention generally relates to the field of specimen analysis and, more particularly, to a system and method for improving image quality of specimens utilizing machine learning techniques.

BACKGROUND

With ever-decreasing feature sizes of electronic logic and memory devices presents a wide range of manufacturing challenges. For example, in the context of semiconductor fabrication, identifying defects from semiconductor devices is an important step in improving throughput and yield. As feature sizes decrease, inspection becomes critical to suc-cessful manufacturing and ever-smaller defects may cause device failure. With shrinking design rules, semiconductor manufacturing processes may operate closer to the bound-aries of the capabilities of the technology.

Current approaches to optically imaging, resolving, and analyzing small features is limited by the optical resolution of the imaging system being used.

Further, methods to obtain more detailed images of the features, such as through a second, follow-up imaging pass using a scanning electron microscope (SEM) may be time consuming and impracticable to perform for analysis of hundreds of features.

In addition, traditional techniques may attempt to increase the resolution of the optical images using machine learning with higher resolution SEM images but may be difficult, time consuming, and expensive to create training data for.

Therefore, it would be desirable to provide a system and method that cures one or more of the shortfalls of the previous approaches identified above.

SUMMARY

A characterization system for enhancing image quality is disclosed, in accordance with one or more embodiments of the present disclosure. In one illustrative embodiment, the system includes one or more controllers including one or more processors configured to execute a set of program instructions maintained in a memory. In another illustrative embodiment, the set of program instructions are configured to cause the one or more processors to acquire a machine learning model trained for correlating one or more training images and one or more training design images. In another illustrative embodiment, the set of program instructions are configured to cause the one or more processors to receive one or more sample specimen images corresponding to one or more features of a sample specimen. In another illustra-tive embodiment, the set of program instructions are con-figured to cause the one or more processors to enhance the one or more sample specimen images by generating one or more enhanced images with the machine learning model based on at least the one or more sample specimen images.

A method for enhancing image quality is disclosed, in accordance with one or more embodiments of the present disclosure. In one illustrative embodiment, the method includes acquiring a machine learning model trained for correlating one or more training images and one or more training design images. In another illustrative embodiment, the method includes receiving one or more sample specimen images corresponding to one or more features of a sample specimen. In another illustrative embodiment, the method includes enhancing the one or more sample specimen images by generating one or more enhanced images with the machine learning model based on at least the one or more sample specimen images.

It is to be understood that both the foregoing general description and the following detailed description are exem-plary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures.

FIG. 3A illustrates a flowchart for training a machine learning model, in accordance with one or more embodi-ments of the present disclosure.

FIG. 5 illustrates a flowchart of a method for enhancing image quality utilizing a machine learning model, in accor-dance with one or more embodiments of the present disclo-sure.

DETAILED DESCRIPTION

Figure 1:
FIG. 1 illustrates a flowchart for identifying defects using SEM images.

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Reference will now be made in detail to the subject matter disclosed, which is illustrated in the accompanying drawings.

Referring generally to FIGS. 1 through 5, systems and methods for enhancing image quality are disclosed, in accordance with one or more embodiments of the present disclosure. Embodiments of the present disclosure are directed to acquiring a machine learning model trained for correlating one or more training images and one or more training design images. Additional embodiments are directed to enhancing one or more sample specimen images by generating one or more enhanced images with the machine learning model based on at least the one or more sample specimen images.

It is noted herein that it may be possible to render SEM images using 3D design images. For example, rendering SEM images using 3D design images is described generally in U.S. patent application Ser. No. 16,564,981 filed on Sep. 9, 2019, which is incorporated herein by reference in its entirety. However, it is contemplated herein that this approach may have limitations. For example, rendering SEM images using 3D design images may require that an SEM be used during a training process and that 3D design images be available at runtime (e.g., while using the machine learning model). However, obtaining SEM images for training may be prohibitively expensive and slow to perform. Further, 3D design images may not be readily available at runtime. In addition, the generated SEM images, based on 3D design images, may be limited in their ability to identify/predict features and characteristics (e.g., incapable of predicting defects) because the 3D designs are not actual real-world images of manufactured specimens with the particular real-world features (e.g., defects) to be predicted, identified, and/or enhanced.

Some embodiments are directed to systems and methods enhancing image quality that addresses at least some of these concerns.

For example, in some applications, it may be possible to provide a characterization system that uses optical images, not SEM images. In this example, the optical images may be used in training (along with design images) and as input to be enhanced by a machine learning model. For instance, a training data set of many (e.g., thousands) of training pairs of training images and training design images may be quickly, inexpensively, and accurately (e.g., accurately aligned) created, generated, received, or the like. SEM imaging is often slow and expensive.

Further, when enhancing sample specimen images (e.g., optical images) real-world data is obtained (e.g., the optical images are real-world data) and enhanced to provide for more accurate characterization of features of the specimen. On the other hand, 3D design files are not necessarily real-world captured data, and may be data of a predicted specimen. Further, 3D design files may be hard to obtain during an enhancement of sample specimen images (e.g., while running the machine learning model) while the specimen itself may be readily available to be imaged.

FIG. 1 illustrates for a series of images depicting a traditional defect identification technique. In order to analyze the relative location, type, and structure of features (e.g., defects) within a specimen (e.g., semiconductor wafer), traditional techniques may first obtain one or more optical images 102, as shown in FIG. 1. For example, as shown in FIG. 1, optical images 100 of a wafer patterned with EUV lithography are shown. Further, SEM images 104 are shown of the same areas of the same wafer below each corresponding optical image 102. It is noted that when a probable defect is predicted to be somewhere in an area of interest 106, it may be extremely difficult to determine which exact feature (e.g., polygon feature 108) is failing in that area of interest 106 based on an optical image 102 alone. This is because the features 108 in optical images 102 may not be fully resolved optically, as shown by optical images 102. Rather, it may be that only after follow-up imaging from an SEM is taken (as shown by SEM images 104) that the particular polygon feature 108 that failed is identifiable (e.g., which may have failed due to EUV stochastic hotspot as shown in FIG. 1). However, it is noted that follow-up imaging on an SEM to obtain the SEM images 104 shown in FIG. 1 may be slow, expensive, and impracticable to perform for each area of interest 106 (e.g., prohibitively time consuming or expensive, compared to obtaining optical images 102). It is noted that embodiments of the present disclosure allow for the ascertainment of the nature, and/or context of a feature (e.g., defect) imaged by an imaging tool (e.g., inspector) without SEM review (e.g., follow-up).

Accordingly, embodiments of the present disclosure are directed to a system and method which cure one or more of the shortfalls of previous approaches identified above.

Figure 2A:
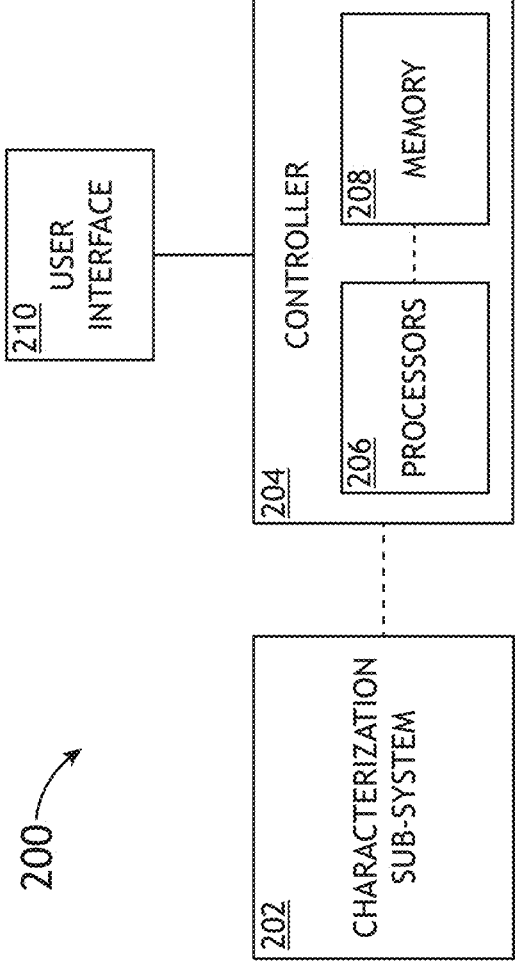
FIG. 2A illustrates a characterization system utilizing machine learning techniques to generate enhanced images of a specimen, in accordance with one or more embodiments of the present disclosure.

FIG. 2A illustrates a characterization system 200 utilizing machine learning techniques to generate enhanced images of a specimen, in accordance with one or more embodiments of the present disclosure. The system 200 may include, but is not limited to, one or more characterization sub-systems 202. The system 200 may additionally include, but is not limited to, a controller 204 including one or more processors 206 and a memory 208, and a user interface 210.

The characterization sub-system 202 may include any characterization sub-system 202 known in the art including, but not limited to, an optical-based characterization system. In one embodiment, the controller 204 is communicatively coupled to the one or more characterization sub-systems 202. In this regard, the one or more processors 206 of the controller 204 may be configured to generate one or more control signals configured to adjust one or more characteristics of the characterization sub-system 202.

Figure 2B:
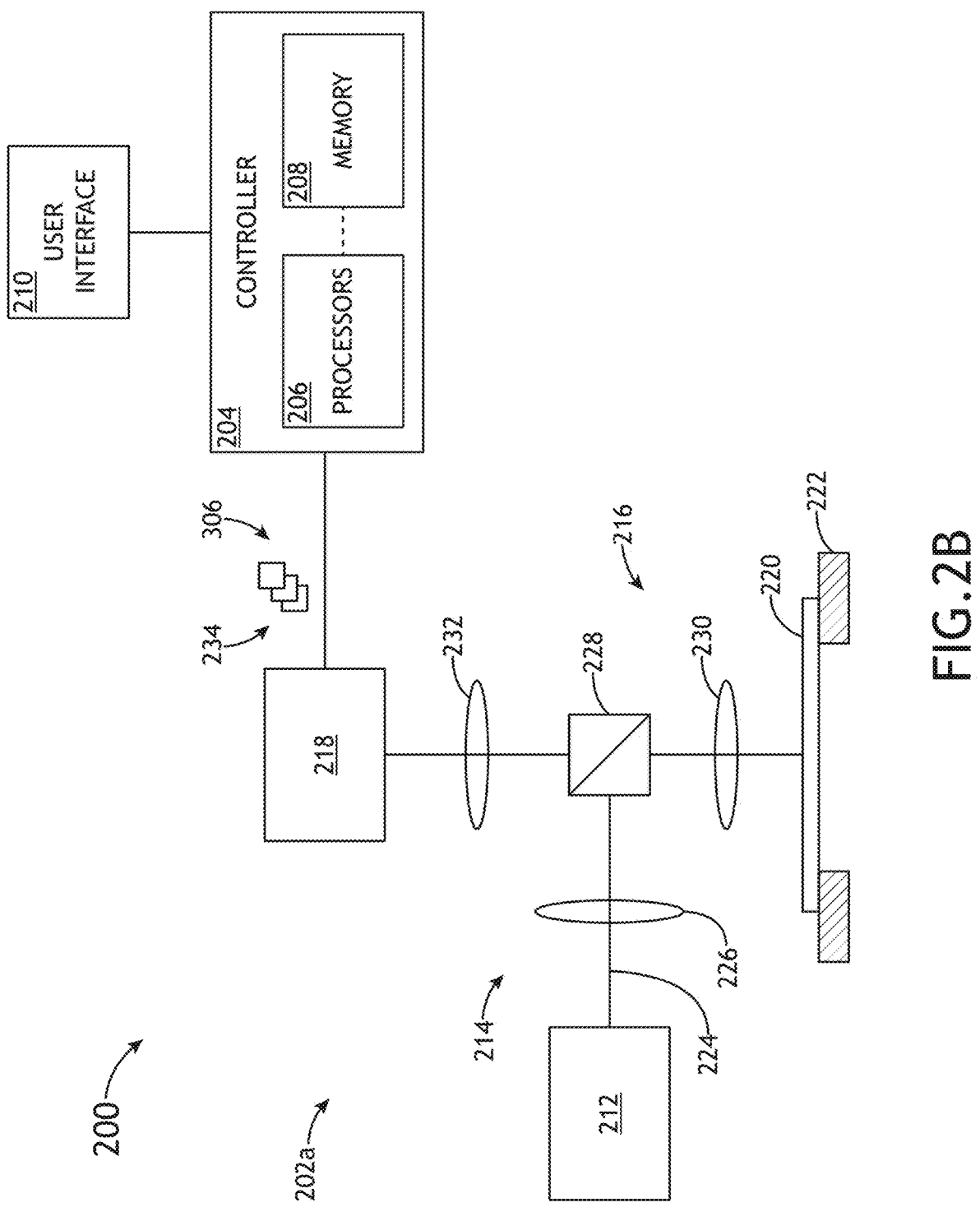
FIG. 2B illustrates a characterization system utilizing machine learning techniques to generate enhanced images of a specimen, in accordance with one or more embodiments of the present disclosure.

FIG. 2B illustrates a characterization system 200 utilizing machine learning techniques to generate enhanced images of a specimen, in accordance with one or more embodiments of the present disclosure. In particular, FIG. 2B illustrates a characterization system 200 including an optical characterization sub-system 202a.

The optical characterization sub-system 202a may include any optical-based characterization system known in the art including, but not limited to, an optical inspection tool or an image-based metrology tool. For example, the characterization sub-system 202a may include an optical inspection tool that allows for inspection of defects. In another example, the characterization sub-system 202a may include an optical critical dimension metrology tool. The optical characterization sub-system 202a may include, but is not limited to, an illumination source 212, an illumination arm 214, a collection arm 216, and a detector assembly 218.

In one embodiment, optical characterization sub-system 202a is configured to inspect and/or measure the specimen 220 disposed on the stage assembly 222. Illumination source 212 may include any illumination source known in the art for generating illumination 224 including, but not limited to, a broadband radiation source. In another embodiment, optical characterization sub-system 202a may include an illumination arm 214 configured to direct illumination 224 to the specimen 220. It is noted that illumination source 212 of optical characterization sub-system 202a may be configured in any orientation known in the art including, but not limited to, a dark-field orientation, a light-field orientation, and the like.

Specimen 220 may include any specimen known in the art including, but not limited to, a wafer (e.g., semiconductor wafer), a reticle, a photomask, and the like. In one embodiment, specimen 220 is disposed on a stage assembly 222 to facilitate movement of specimen 220. In another embodiment, the stage assembly 222 is an actuatable stage. For example, the stage assembly 222 may include, but is not limited to, one or more translational stages suitable for selectably translating the specimen 220 along one or more linear directions (e.g., x-direction, y-direction and/or z-direction). By way of another example, the stage assembly 222 may include, but is not limited to, one or more rotational stages suitable for selectively rotating the specimen 220 along a rotational direction. By way of another example, the stage assembly 222 may include, but is not limited to, a rotational stage and a translational stage suitable for selectably translating the specimen 220 along a linear direction and/or rotating the specimen 220 along a rotational direction. It is noted herein that the system 200 may operate in any scanning mode known in the art.

The illumination arm 214 may include any number and type of optical components known in the art. In one embodiment, the illumination arm 214 includes one or more optical elements 226, a beam splitter 228, and an objective lens 230. In this regard, illumination arm 214 may be configured to focus illumination 224 from the illumination source 212 onto the surface of the specimen 220. The one or more optical elements 226 may include any optical elements known in the art including, but not limited to, one or mirrors, one or more lenses, one or more polarizers, one or more beam splitters, and the like.

In another embodiment, optical characterization sub-system 202a includes a collection arm 216 configured to collect illumination reflected or scattered from specimen 220. In another embodiment, collection arm 216 may direct and/or focus the reflected and scattered light to one or more sensors of a detector assembly 218 via one or more optical elements 232. The one or more optical elements 232 may include any optical elements known in the art including, but not limited to, one or mirrors, one or more lenses, one or more polarizers, one or more beam splitters, and the like. It is noted that detector assembly 218 may include any sensor and detector assembly known in the art for detecting illumination reflected or scattered from the specimen 220.

In another embodiment, the detector assembly 218 of the optical characterization sub-system 202 is configured to collect image data of the specimen 220 based on illumination reflected or scattered from the specimen 220. In another embodiment, the detector assembly 218 is configured to transmit collected/acquired images and/or metrology data to the controller 204.

As noted previously herein, the controller 204 of system 200 may include one or more processors 206 and memory 208. The memory 208 may include program instructions configured to cause the one or more processors 206 to carry out various steps of the present disclosure. In one embodiment, the program instructions are configured to cause the one or more processors 206 to adjust one or more characteristics of the optical characterization sub-system 202 in order to perform one or more measurements of the specimen 220.

In another embodiment, as shown in FIG. 2A and FIG. 2B, system 200 includes a user interface 210 communicatively coupled to the controller 204. In another embodiment, the user interface 210 includes a user input device and a display. The user input device of the user interface 210 may be configured to receive one or more input commands from a user, the one or more input commands configured to input data into system 200 and/or adjust one or more characteristics of system 200. In another embodiment, the display of the user interface 210 may be configured to display data of system 200 to a user.

As noted previously herein, the one or more processors 206 of the controller 204 may be communicatively coupled to memory 208, wherein the one or more processors 206 may be configured to execute a set of program instructions maintained in memory 208, and the set of program instructions may be configured to cause the one or more processors 206 to carry out various functions and steps of the present disclosure. In this regard, the controller 204 may be configured to: acquire, with the characterization sub-system 202, one or more training images 234 comprising one or more training features (e.g., polygon features 108) of a one or more training specimens 220; receive the one or more training design images 302 corresponding to the one or more training features of the one or more training specimens 220; aligning the one or more training images 234 with one or more training design images 302 corresponding to the one or more training features of the one or more training specimens 220; generating a machine learning model based on the one or more training images 234 and the one or more training design images 302; receive one or more sample specimen images 306 corresponding to one or more features of a sample specimen; and enhance the one or more sample specimen images 306 by generating one or more enhanced images 308 with the machine learning model based on at least the one or more sample specimen images 306.

Figure 3A:
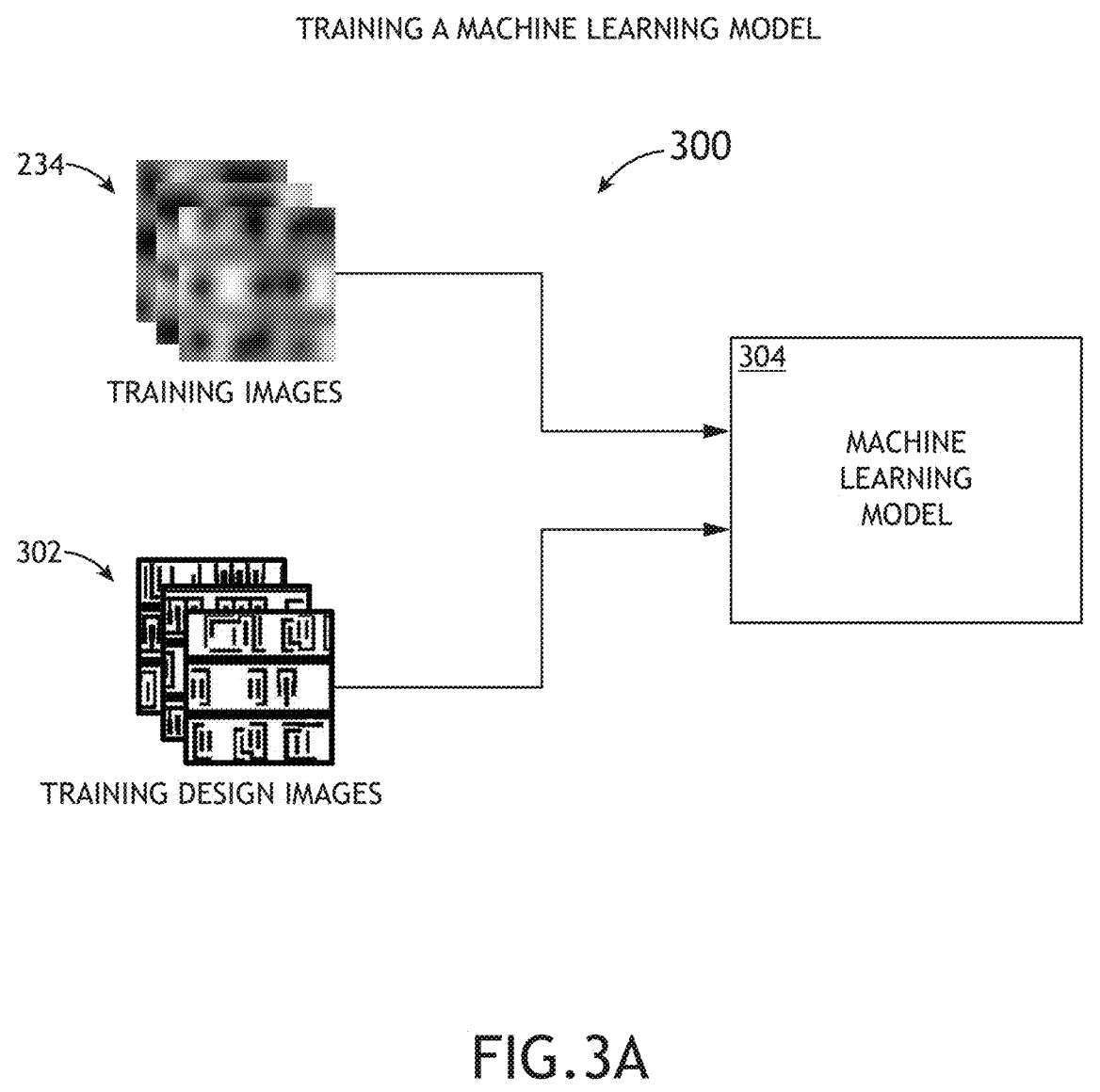

FIG. 3A illustrates a flowchart 300 for training a machine learning model, in accordance with one or more embodiments of the present disclosure. In this regard, flowchart 300 may be considered a conceptual flowchart illustrating steps performed by/within the one or more processors 206 of the controller 204.

In one embodiment, the controller 204 is configured to receive one or more training images 234 of one or more training features of a training specimen 220 from the characterization sub-system 202. For the purposes of the present disclosure, the term "training images" and the like may be regarded as images which will be used as inputs to train a machine learning classifier (e.g., machine learning model).

For example, as shown in FIG. 3A, the controller 204 may be configured to receive one or more optical training images 234 of one or more features of the specimen 220 from the optical characterization sub-system 202a. In this regard, the training images 234 depicted in FIG. 3A may include an optical training image 234. In additional and/or alternative embodiments, the controller 204 may be configured to receive one or more training images 234 from a source other than the one or more characterization sub-systems 202. For example, the controller 204 may be configured to receive one or more training images 234 of features of a specimen 220 from an external storage device and/or memory 208. In another embodiment, controller 204 may be further configured to store received training images 234 in memory 208.

In another embodiment, the controller 204 is configured to receive one or more training design images 302 corresponding to the one or more features of the specimen 220. The term "training design image 302," and like terms, may be regarded as any data, file, or image associated with a design (or derived from a design) of a specimen 220 (e.g., training specimen). In this regard, the term "design image"

may be used interchangeably with the terms "design data," "design-derived data," "design file," and "design-derived file." A design of a specimen may be a chip design. The design data may be in 2D format, which may be a single layer. In another example, the design data may be multi-layer design images, such as multi-layer 3D design images of two or more layers of a design of two or more layers of a sample. In another example, "design image" may be an image derived from design data such as an image derived from a simulated physical model or geometric transforma-tions of design data. For instance, a design of the specimen may be modified through geometric transformations that may, in some embodiments, be configured to modify the design such that the design is more conducive to being used as training data of a machine learning model. In this regard, the design of the specimen may be modified through geo-metric transformations that round the corners and/or edges of the design and/or make the edges blurred. In some embodiments, the one or more training design images 302 are stored in memory 208 such that the controller 204 is configured to receive and/or retrieve the one or more train-ing design images 302 from memory 208.

In one embodiment, the controller 204 is configured to align one or more training images 234 with one or more training design images 302. It is noted that aligning the one or more training images 234 with one or more training design images 302 may be performed by a system capable of a high alignment accuracy. For example, alignment may be performed (or made possible) by a characterization system 200 that is configured to be capable of alignment within a few pixels of accuracy (e.g., sub-pixel accuracy). It should be noted, in some embodiments, that having some training pairs (e.g., a training image 234 aligned with a training design image 302) with alignment accuracy error within a few pixels is not only acceptable, but may help to regularize the machine learning model and thus prevent overfitting of the machine learning model. One metric of alignment quality is a defect-based pattern to design align-ment (PDA) quality. In some embodiments, the PDA quality may be used to control the alignment accuracy of the training set (i.e., set of training pairs).

In some embodiments, once a training pair is aligned, one or more modifications may be made to each training pair in order to increase the size of the training data set (i.e., set of training pairs). Such modifications may allow for a more accurate and/or more robust machine learning model. For example, modifications may include changing the orienta-tions of the training pairs and flipping the training pair images to produce rotated and/or flipped versions.

It is noted that the benefits of alignment include but are not limited to quickly generating a large, low-cost training set of training pairs of aligned training images 234 and training design images 302. For example, thousands of training pairs may be obtained with relative ease by a quick scan of a wafer using an inspector or target acquisition of a metrology tool. For instance, if the optics of an imaging tool (e.g., metrology tool) are set to a Best Known Method (BKM) setting for a given layer of a wafer, no sensitivity parameter tuning, defect verification, or SEM review is required to create, generate, receive, or the like a large training data set of training pairs.

Further, it is noted that benefits of the embodiments of this disclosure may include, but are not limited to: allowing for fast and relatively low-cost acquiring of optical images for use during the training and use (e.g., enhancing) of a machine learning model (discussed in detail throughout this disclosure); allowing for fast and relatively low-cost receiving (or generating, or the like) of training design images for use during the training of a machine learning model; quickly and/or cost-effectively aligning the training images and the training design images; and, for example, not requiring a slow and expensive SEM follow-up pass to collect training SEM images for a machine learning model based on SEM images.

In some embodiments, alignment may be performed (or made possible) by an optical inspection and/or metrology system capable of handling design files such as .gds files and/or .oas files.

In some embodiments, aligning the training images and the training design images may allow for the training design images to be a high-resolution ground truth of a specimen, which may allow for enhancing the image quality of images similar to the training images (e.g., of similar specimens). In some embodiments, such enhancement may allow for super-resolution of images and better computation of context parameters of a feature (e.g., defect), localization or tagging of a feature, and more accurate classification of subtle features, and may also offer a new approach to detect/redetect defects with improved signal to noise (SNR) ratios. For example, the resolution of an enhanced image may be higher than the resolution of the training images and/or the sample specimen image.

In another embodiment, the controller 204 is configured to generate a machine learning model 304 based on the one or more training images 234 and the one or more training design images 302. In this regard, the one or more training images 234 and the one or more training design images 302 may be used as inputs to train the machine learning model 304. The machine learning model 304 may include any type of machine learning algorithm/classifier and/or deep learn-ing technique or classifier known in the art including, but not limited to, generative adversarial network (GAN), a condi-tional generative adversarial network (CGAN), a convolu-tional neural network (CNN) (e.g., GoogleNet, AlexNet, and the like), an ensemble learning classifier, a random forest classifier, artificial neural network (ANN), auto-encoders, and the like. In embodiments, the controller 204 may be configured to store the generated machine learning model 304 in memory 208.

Figure 3B:
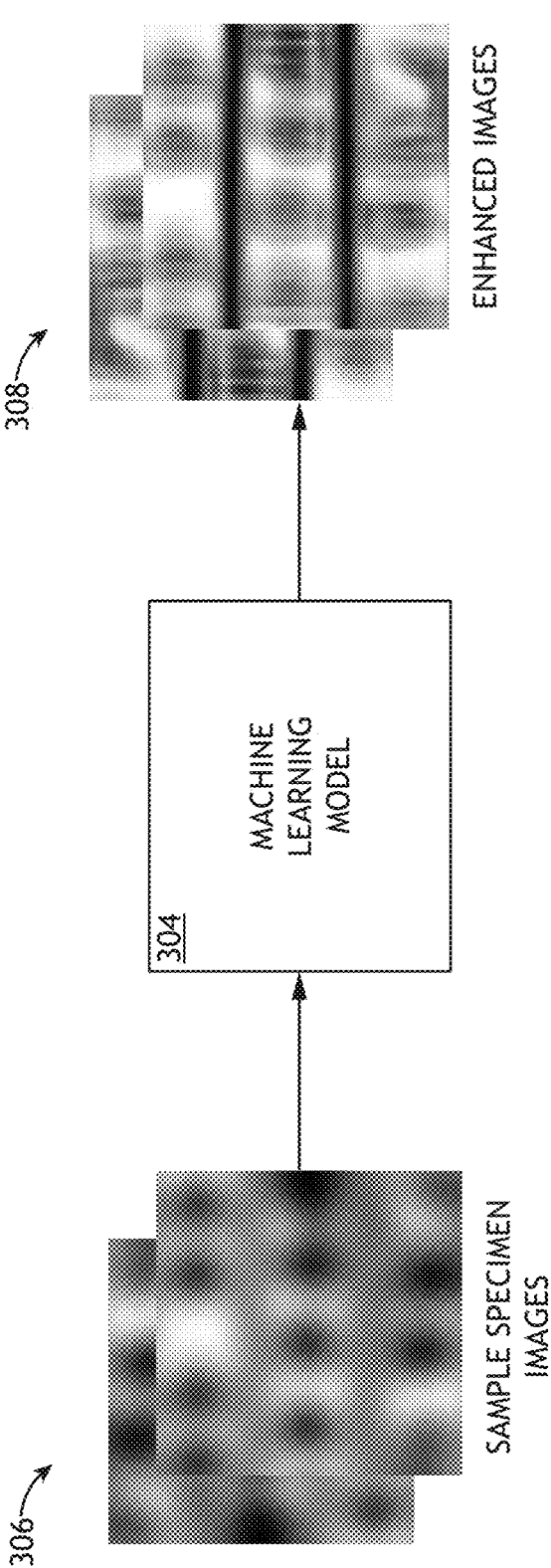
FIG. 3B illustrates a flowchart of a trained machine learning model configured to generate enhanced images of a specimen based on specimen images of the specimen, in accordance with one or more embodiments of the present disclosure.

It is contemplated herein that the controller 204 may be configured to generate the machine learning model 304 via supervised learning and/or unsupervised learning. Training/generating the machine learning model 304 may include teaching the machine learning model 304 to generate enhanced images 308 based on sample specimen images 306, as shown in FIG. 3A. In this regard, the machine learning model 304 may include any algorithm, classifier, or predictive model configured to generate enhanced images 308 (as shown in FIG. 3B). This will be discussed in further detail herein. It should be known that the enhanced images 308 shown in FIG. 3B are for illustrative purposes only and may be under optimized and thus less than a full display of the potential output of a machine learning model provided for by at least some embodiments of this disclosure.

In one embodiment, after the machine learning model 304 has been trained, the controller 204 may be configured to receive one or more sample specimen images 306 of one or more features of a sample specimen 220. As it is used herein, the term "sample images" (e.g., "sample" specimen images 306) or the like may be used to refer to sample images of a sample specimen which are not used to train the machine learning model 304. More specifically, for example, sample specimen images 306 may refer to images of a sample specimen 220 of a fabrication/characterization process for which enhanced images 308 are desired. For example, sample specimen images 306 may include optical images of a sample specimen 220 which is to be fabricated in a fabrication process. As noted previously, the one or more product sample specimen images 306 may be stored in memory 208 such that the controller 204 is configured to receive and/or retrieve the one or more sample specimen images 306 from memory 208.

In embodiments, the one or more features of the specimen 220 may include any features which may be of interest throughout a specimen 220 fabrication/characterization process including, but not limited to, patterned structures, defects, high aspect ratio (HAR) structures, critical dimension (CD) structures, and the like. For example, when designing a specimen 220 which is to be fabricated, a process engineer may know the relative location, type, and rough structure of a defect which is likely to be created during the fabrication of the specimen 220. In order to predict what optical images of the probable defect may look like in order to more efficiently identify the defects after creation, the process engineer may generate training design images 302 of the probable defect at various locations. The various locations may be known defect locations from library, inputs by process or design teams, or inspection output of an inspector (which may be a probable defect location). These training design images 302 may then be input to the machine learning model 304 to train the machine learning model.

In another embodiment, the controller 204 is configured to generate one or more enhanced images 308 of the one or more features of the specimen 220 based on the one or more sample specimen images 306 with the machine learning model 304. For example, continuing with the same example above, one or more sample specimen images 306 of a probable defect (e.g., feature) within a sample specimen 220 may be input to the machine learning model 304. The controller 204 may be configured to receive these sample specimen images 306 of the probable defect (e.g., which may include its location), and generate one or more enhanced images 308 of the probable defect (e.g., feature) (e.g., at the same location) with the machine learning model 304. In embodiments, the machine learning model 304 may be configured to generate enhanced optical images (e.g., enhanced images 308) of the probable defect. The enhanced images may appear to be, but not limited to, a design image (e.g., derived design image) or an approximation of a design image. The controller 204 may be configured to store the one or more enhanced images 308 in memory 208.

Enhancement may include but is not limited to (i.e., the enhanced images may possess enhanced characteristics relative to the sample specimen images): higher resolution (e.g., super-resolution); higher clarity/ability to resolve (e.g., less blurry); higher contrast; higher signal to noise ratio; and higher sensitivity of features or characteristics of features. For example, one or more features of an image (e.g., sample specimen image 306) may be sub-resolution (e.g., less than one pixel and/or not resolvable) in size and the resolution of an enhanced image 608 may be improved such that at least one of the one or more features is not sub-resolution in size.

In embodiments, the enhanced images 308 generated by the machine learning model 304 may be used as reference images for subsequent characterization, inspection, and detection. For example, by generating enhanced images 308 of a defect, a user and/or the system 200 may be configured to recognize/identify probable characteristics of the defect (e.g., defect localization, defect context attributes, classification scheme of defects, defect classification type, defect size, and the like). When a specimen 220 is subsequently inspected, the system 200 may be configured to more quickly and efficiently identify the defect based on the known probable characteristics of the defect identified within the enhanced images 308.

In another embodiment, the controller 204 is configured to determine one or more characteristics of the specimen 220 based on the one or more enhanced images 308. Continuing with the same example above, the controller 204 may be configured to determine one or more characteristics of the probable defect (e.g., feature) of the sample specimen 220 based on the enhanced images 308. Characteristics of the specimen 220 and/or features of the specimen 220 which may be determined based on the enhanced images 308 may include any characteristic of a specimen 220 known in the art including, but not limited to, a location of a defect within the specimen 220, a type of defect within the specimen 220, a context attribute of the defect, a classification scheme of the defect, a size of the defect, measurement of the specimen 220, and the like.

Figure 4:
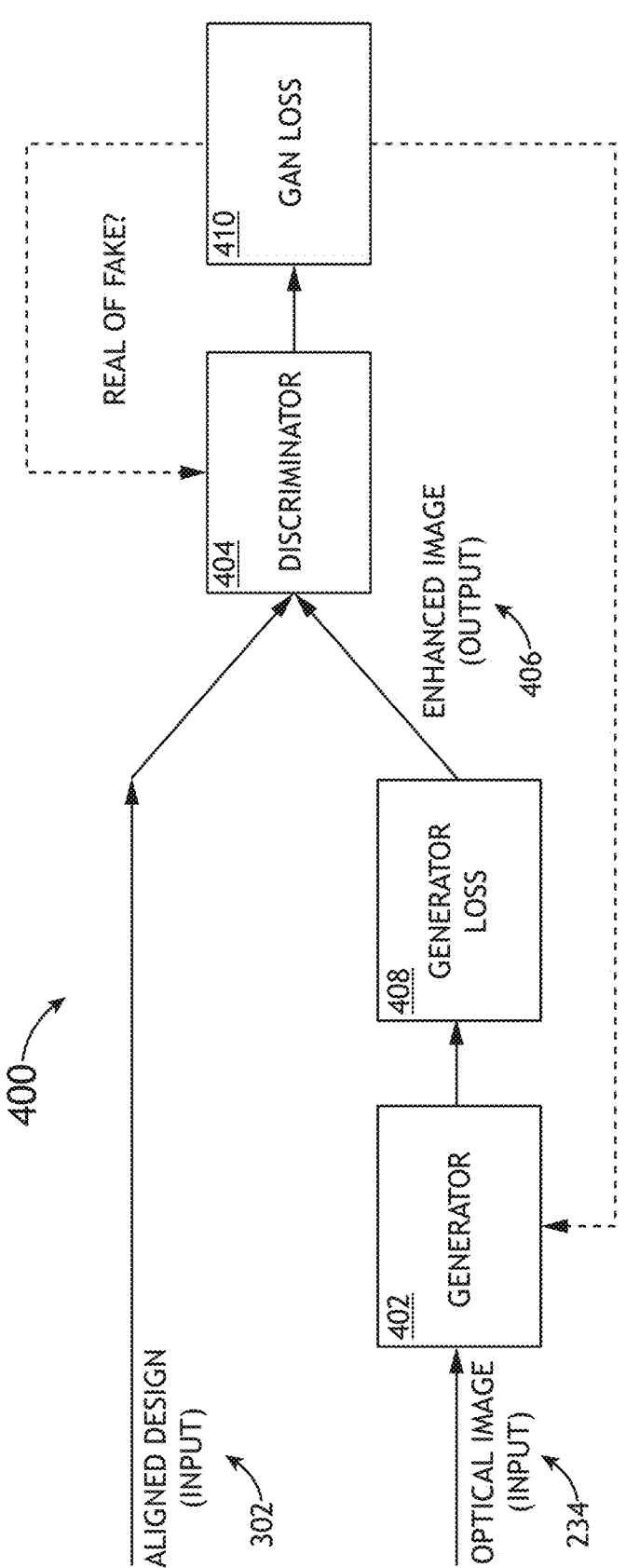
FIG. 4 illustrates a flowchart for training a machine learning model including a generative adversarial network (GAN), in accordance with one or more embodiments of the present disclosure.

FIG. 4 illustrates a flowchart 400 for training a machine learning model, in accordance with one or more embodiments of the present disclosure. It is noted that FIG. 4 may depict a generic flowchart 400 for training a GAN, but that FIG. 4 is provided for illustrative purposes only, and is not to be considered a limitation of the types or structure of machine learning models of this disclosure. In some embodiments, the machine learning model 304 may be a deep learning model 304. In some embodiments, the machine learning model 304 may be a generative adversarial network (GAN) 304. In embodiments, a GAN 304 (e.g., machine learning model 304) may include, but is not limited to, a generator 402 and a discriminator 404. In embodiments, the generator 402 may be configured to generate enhanced images 406 from training images 234 (e.g., "real" optical image of a specimen 220) during training. The discriminator 404 may be configured to receive a training design image 302 (e.g., design image aligned to the training image 234) and an enhanced image 406 (e.g., generated from input optical images) and determine whether each enhanced image is similar to a design image. Determinations of "similar" or "not similar" may be referred to as discriminator outputs. In this regard, training the GAN (e.g., machine learning model 304) may involve training the discriminator 404 to become more accurate in identifying enhanced optical images very similar to design, as well as training the generator 402 to generate more realistic "high resolution (or enhanced) optical" images to "trick" the discriminator 404. As the discriminator 404 becomes better at deciphering between training design images 302 and generated enhanced images 406, the generator 402 must become better at generating more realistic enhanced optical images 406. When training the GAN, a GAN loss 410 may be determined and the GAN loss 410 may be used to update (e.g., update the weights) of the generator 402 and the discriminator 404. A generator loss 408 may also be determined and used as input to the discriminator 404. After the generator 402 has been sufficiently trained, the enhanced images 406 may be output from the machine learning model 304 as the enhanced images 308 illustrated in FIG. 3B. Note that training images 234 in FIG. 3A may be or comprise training design images 302 in FIG. 3B.

FIG. 5 illustrates a flowchart of a method 500 for enhancing image quality utilizing a machine learning model 304, in accordance with one or more embodiments of the present disclosure. It is noted herein that the steps of method 500 may be implemented all or in part by characterization system 200. It is further recognized, however, that the method 500 is not limited to the characterization system 200 in that additional or alternative system-level embodiments may carry out all or part of the steps of method 500.

In a step 502, one or more training images of one or more features of one or more training specimens are acquired with a characterization sub-system. For example, as shown in FIG. 3A, the controller 204 may be configured to receive one or more optical training images 234 of one or more features of one or more specimens 220 from the optical characterization sub-system 202*a*.

In a step 504, one or more training design images corresponding to one or more features of the specimen are received. For example, the one or more training design images 302 may be stored in memory 208 such that the controller 204 is configured to receive and/or retrieve the one or more training design images 302 from memory 208.

In a step 506, one or more training images are aligned with one or more training design images corresponding to the one or more training features of the one or more training specimens. For example, the one or more training design images 302 may be stored in memory 208 such that the controller 204 is configured to receive and/or retrieve the one or more training design images 302 from memory 208. In another example, the one or more training design images 302 may be aligned in real-time. For instance, the one or more training design images 302 may be mathematically aligned using a pixel to design alignment.

In a step 508, a machine learning model is generated based on the one or more training images and the one or more training design images. For example, the one or more training images 234 and the one or more training design images 302 may be used as inputs to train the machine learning model 304. The machine learning model 304 may include any type of machine learning algorithm/classifier and/or deep learning technique or classifier known in the art including, but not limited to, a conditional generative adversarial network (CGAN), a convolutional neural network (CNN) (e.g., GoogleNet, AlexNet, and the like), an ensemble learning classifier, a random forest classifier, artificial neural network (ANN), auto-encoders, and the like.

It should be noted that the one or more training design images 302 may be labeled (e.g., features of the one or more training design images may be labeled to enhance training).

In an alternative step (not shown), steps 502 through 508 may be alternatively replaced by a step. In such a step a machine learning model may be acquired or received, the machine learning model based on one or more training images and one or more training design images corresponding to and aligned with the one or more training images. For example, the controller 204 may be configured to acquire a machine learning model based on one or more training images and one or more training design images corresponding to and aligned with the one or more training images. For example, the machine learning model may be generated by a different system. In another example, within a method or the controller 204 may be configured to acquire a machine learning model trained for correlating one or more training images and one or more training design images.

In a step 510, one or more sample specimen images corresponding to one or more features of a sample specimen are received. For example, as shown in FIG. 2B and FIG. 3B, the controller 204 may be configured to receive one or more sample specimen images 306 of one or more features of a sample specimen 220.

In a step 512, the one or more sample specimen images are enhanced by generating one or more enhanced images with the machine learning model based on at least the one or more sample specimen images. For example, as shown in FIG. 3B, the controller 204 may be configured to enhance one or more sample specimen images 306 of a feature (e.g., probable defect) by generating one or more enhanced images 308 with the machine learning model 304 based on at least the one or more sample specimen images 306.

In an optional step 514, one or more characteristics of the specimen are determined based on the one or more enhanced images. For example, continuing with the same example, the controller 204 may be configured to determine one or more characteristics of the feature (e.g., probable defect) of the sample specimen 220 based on the generated enhanced images 308. Characteristics of the sample specimen 220 and/or features of the sample specimen 220 which may be determined based on the enhanced images 308 may include any characteristic of a specimen known in the art including, but not limited to, a location of a feature (e.g., defect) within the specimen 220, a type of feature within the specimen 220, a context attribute of the feature, a classification scheme of the feature, a size of the feature, and measurement of the feature or specimen 220, and the like.

In an optional step (not shown), a process tool may be adjusted based on the one or more characteristics. For example, feedforward and/or feedback may be used to adjust a process tool (e.g., lithography tool) on a fabrication line to at least mitigate defects in the current sample (in the case of feedforward) or avoid defects in subsequent samples (in the case of feedback). In this regard, the controller 204 may transmit a control signal to a process tool that causes the process tool to adjust one or more parameters. This adjustment may be performed upstream (in the case of feedback) to adjust process tool parameters with respect to subsequent samples and/or may be performed downstream (in the case of feedforward) to adjust process tool parameters with respect to the current sample. For instance, continuing with the same example, the controller 204 may be configured to adjust a process tool based on the one or more characteristics. The characterization system 200 may be or include an imaging tool/system. For example, the characterization system 200 may be an inspection tool. In another example, the characterization system 200 may be an overlay metrology tool. The process tool may be any tool used in the manufacture or inspection of a sample. For example, the process tool may be a lithography tool, an SEM review tool, or the like.

In an optional step (not shown), a metrology tool may be adjusted based on the one or more characteristics. For example, a metrology tool (e.g., overlay metrology tool) may be adjusted based on a characteristic of a defect or measurement determined on an enhanced image generated by the machine learning model.

In an optional step (not shown), context attributes may be used to determine a feature (e.g., defect) classification type. For example, the controller 204 may be configured to determine whether a classification type of a defect is one of at least a Defect of Interest (DOI) or a nuisance defect. It is noted that a nuisance defect may be a "false" defect (e.g., a defect that does not affect specimen performance or yield). A DOI may be a defect that does affect performance and/or yield.

It should be noted that determining a characteristic or the like (e.g., one or more characteristics of one or more features) in this disclosure means determining a characteristic for the first time as well as determining a characteristic in such a way that a known (pre-existing) characteristic may be updated/refined. For example, determining a localization may mean updating/refining a pre-existing localization.

For example, it should be noted determining a characteristic that is a localization may include determining a more accurate location. A location may be relative to the characteristic system 200, any element of the characteristic system 200, a coordinate system used by the controller 204, or any other relative location coordinate system. It should be noted that more accurate localization is beneficial for use at least in multi-patterning schemes for polygon layer tagging, and stochastics identification in EUV patterning (e.g., see FIG. 1).

For example, it should be that determining a characteristic that is a classification scheme may include determining a more accurate classification scheme. A classification scheme may include, but is not limited to, a scheme for classifying features (e.g., defects). For example, any number of attributes (e.g., a combination of size, shape, surroundings, and any other attribute) of a feature may be used to classify that feature in one or more categories (e.g., DOI or nuisance defect).

For example, it should be that determining a characteristic that is a classification type may include determining a more accurate classification type. For example, the controller 204 may be configured to determine whether a classification type of a feature is accurate and refine the classification type determination of that feature. For instance, the controller 204 may be configured to update a pre-determined classification type of a feature to a different classification type (e.g., change the classification type from DOI to nuisance defect or vice versa).

For example, it should be that determining a characteristic that is a size (e.g., size measurement) may include determining a more accurate size and/or updating/refining a size. For example, an enhanced image may have improved quality of resolution and ability to resolve features, which may allow for improved measurement accuracy.

In an optional step (not shown), one or more defects may be re-identified based on the one or more enhanced images. For example, the controller 204 may be configured to re-identify one or more defects based on the one or more enhanced images. Re-identifying may mean, but is not limited to, identifying after a first identification that may have occurred using a different system or method or the same or similar characterization system 200 and method disclosed throughout.

In an optional step (not shown), one or more defects may be identified based on the one or more enhanced images. For example, the controller 204 may be configured to identify (e.g., first identification) one or more defects based on the one or more enhanced images.

It should be noted that enhancing the one or more sample specimen images by generating one or more enhanced images, and/or identifying (detecting) one or more features (e.g., defects) may be used for re-detection of one or more features (e.g., defects). For example, for re-detection (e.g., re-identification) the machine learning model may be used to both test, and reference patch one or more features (e.g., defects). Continuing with the same example, the one or more features (e.g., defects) may be analyzed (e.g., for determining characteristics) in post processing (e.g., re-detection). In some embodiments, re-detection may create a benefit of more robust distinction between a real defect and a false (e.g., noise) defect.

It should be noted that enhancing the one or more sample specimen images by generating one or more enhanced images, and/or identifying (detecting) one or more features (e.g., defects) may be performed in real-time. For example, enhancing the one or more sample specimen images (e.g., which may be raw optical frame data images used for feature detection) by generating one or more enhanced images with the machine learning model may be performed in real-time (e.g., as in a live scan) or on recorded sample specimen images (e.g., as in VIVA—Virtual Inspector Virtual Analyzer). For instance, identification or detection may occur on a playback of a recorded wafer image during playback.

It should be noted that exact machine learning model details (constructs of various layers of the machine learning model, loss functions, and the like) may be optimized as per a specific problem (e.g., specific feature (e.g., defect) or specimen being analyzed).

It should be noted that training/generating the machine learning model may be performed offline after data for training is collected, but may also be performed in real-time (live) such that as more sample images are recorded (and aligned with design images), the machine learning model may be updated with the recorded training images.

It should be noted that the methods and systems disclosed herein may, in some embodiments, be used offline (e.g., in post process) or during a scan (e.g., in defect detection mode). For example, sample specimen images may be recorded and the identifying one or more defects may occur during at least one of a playback of the recorded sample specimen images or during offline reprocessing of data.

It should be noted that each training defect of two or more training defects of one or more training images may be from a particular Design Based Group (DBG) of two or more different DBGs. DBGs may be groupings of local designs at defect locations returned by an inspection process. Benefits of having training defects from two or more different DBGs may include having a training set (i.e., training images and training design images) with a more diverse design background and a machine learning model that will be more generalized and robust. Such benefits may, in some embodiments, be added at little to no addition expense.

In an optional step (not shown), at least one of the one or more defects may be re-detected (or detected) based on the one or more characteristics of the one or more features. For example, the controller 204 may be configured to re-detect at least one of the one or more defects based on the one or more characteristics of the one or more features. For instance, the re-detection may be performed by the characterization system 200 or any other system or imaging tool (e.g., an SEM). In this regard, a characteristic (e.g., a classification type of DOI) may lead the controller 204 to adjust a process tool (e.g., SEM) to re-detect (e.g., image) a feature based on that feature having a classification of DOI. For example, in at least some embodiments, the present disclosure allows for providing better pareto from optical inspectors and fewer SEM verification. For instance, reducing the number of defects classified as a DOI through the present disclosure may allow for fewer SEM verifications, saving tool time and labor.

Referring again to FIG. 2A, it is noted herein that the one or more components of system 200 may be communicatively coupled to the various other components of system 200 in any manner known in the art. For example, the one or more processors 206 may be communicatively coupled to each other and other components via a wireline (e.g., copper wire, fiber optic cable, and the like) or wireless connection (e.g., RF coupling, IR coupling, WiMax, Bluetooth, 3G, 4G, 4G LTE, 5G, and the like). By way of another example, the controller 204 may be communicatively coupled to one or more components of characterization sub-system 202 via any wireline or wireless connection known in the art.

In one embodiment, the one or more processors 206 may include any one or more processing elements known in the art. In this sense, the one or more processors 206 may include any microprocessor-type device configured to execute software algorithms and/or instructions. In one embodiment, the one or more processors 206 may consist of a desktop computer, mainframe computer system, worksta-tion, image computer, parallel processor, or other computer system (e.g., networked computer) configured to execute a program configured to operate the characterization system 200, as described throughout the present disclosure. It should be recognized that the steps described throughout the present disclosure may be carried out by a single computer system or, alternatively, multiple computer systems. Fur-thermore, it should be recognized that the steps described throughout the present disclosure may be carried out on any one or more of the one or more processors 206. In general, the term "processor" may be broadly defined to encompass any device having one or more processing elements, which execute program instructions from memory 208. Moreover, different subsystems of the characterization system 200 (e.g., illumination source 212, electron beam splitter 228, detector assembly 218, controller 204, user interface 210, and the like) may include processor or logic elements suitable for carrying out at least a portion of the steps described throughout the present disclosure. Therefore, the above description should not be interpreted as a limitation on the present disclosure but merely an illustration.

The memory 208 may include any storage medium known in the art suitable for storing program instructions execut-able by the associated one or more processors 206 and the data received from the characterization sub-system 202. For example, the memory 208 may include a non-transitory memory medium. For instance, the memory 208 may include, but is not limited to, a read-only memory (ROM), a random-access memory (RAM), a magnetic or optical memory device (e.g., disk), a magnetic tape, a solid-state drive and the like. It is further noted that memory 208 may be housed in a common controller housing with the one or more processors 206. In an alternative embodiment, the memory 208 may be located remotely with respect to the physical location of the processors 206, controller 204, and the like. In another embodiment, the memory 208 maintains program instructions for causing the one or more processors 206 to carry out the various steps described through the present disclosure.

In one embodiment, the user interface 210 is communi-catively coupled to the controller 204. The user interface 210 may include, but is not limited to, one or more desktops, tablets, smartphones, smart watches, or the like. In another embodiment, the user interface 210 includes a display used to display data of the system 200 to a user. The display of the user interface 210 may include any display known in the art. For example, the display may include, but is not limited to, a liquid crystal display (LCD), an organic light-emitting diode (OLED) based display, or a CRT display. Those skilled in the art should recognize that any display device capable of integration with a user interface 210 is suitable for implementation in the present disclosure. In another embodiment, a user may input selections and/or instructions responsive to data displayed to the user via a user input device of the user interface 210. For example, a user may view (or a controller may be configured to display) one or more enhanced images 308. For instance, such a displaying of enhanced images may be used (e.g., by a user) in a defect detection or characterization method.

One skilled in the art will recognize that the herein described components (e.g., operations), devices, objects, and the discussion accompanying them are used as examples for the sake of conceptual clarity and that various configu-ration modifications are contemplated. Consequently, as used herein, the specific exemplars set forth and the accom-panying discussion are intended to be representative of their more general classes. In general, use of any specific exem-plar is intended to be representative of its class, and the non-inclusion of specific components (e.g., operations), devices, and objects should not be taken as limiting.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The previous description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

All of the methods described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory.

It is further contemplated that each of the embodiments of the method described above may include any other step(s) of any other method(s) described herein. In addition, each of the embodiments of the method described above may be performed by any of the systems described herein.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effec- tively "associated" such that the desired functionality is achieved. Hence, any two components herein combined to achieve a particular functionality can be seen as "associated with" each other such that the desired functionality is achieved, irrespective of architectures or intermedial com- ponents. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly inter- actable and/or wirelessly interacting components and/or logically interacting and/or logically interactable compo- nents.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "includ- ing but not limited to," the term "having" should be inter- preted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the fol- lowing appended claims may contain usage of the introduc- tory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a con- vention analogous to "at least one of A, B, and C, and the like" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

We claim:

1. A characterization system comprising:

a controller communicatively coupled to a characteriza- tion sub-system, wherein the controller includes one or more processors configured to execute a set of program instructions maintained in memory, wherein the set of program instructions are configured to cause the one or more processors to:

acquire a machine learning model trained for correlating one or more training images and one or more training design images;

receive one or more sample specimen images correspond- ing to one or more features of a sample specimen;

enhance the one or more sample specimen images by generating one or more enhanced images with the machine learning model based on at least the one or more sample specimen images, wherein the one or more enhanced images have improved image quality relative to the one or more sample specimen images, the improved image quality comprising at least one of increased signal-to-noise ratio, increased resolution, or increased contrast; and determine, based on the one or more enhanced images, one or more characteristics of the one or more features, wherein the one or more characteristics of the one or more features comprise a defect classification type of at least one of the one or more features, wherein the defect classification type comprises one of a Defect of Interest (DOI) or a nuisance defect.

2. The characterization system of claim 1, wherein the acquire the machine learning model trained for correlating the one or more training images and the one or more training design images comprises:

acquire, with the characterization sub-system, the one or more training images comprising one or more training features of one or more training specimens;

receive the one or more training design images corre- sponding to the one or more training features of the one or more training specimens;

aligning the one or more training images with the one or more training design images corresponding to the one or more training features of the one or more training specimens;

generating the machine learning model based on the one or more training images and the one or more training design images.

3. The characterization system of claim 1, wherein the acquire the machine learning model trained for correlating the one or more training images and the one or more training design images comprises:

receive the machine learning model, the machine learning model based on the one or more training images and the one or more training design images corresponding to and aligned with the one or more training images.

4. The characterization system of claim 1, wherein the characterization sub-system comprises at least one of an optical inspection sub-system or an optical imaging-based metrology sub-system.

5. The characterization system of claim 1, wherein the one or more characteristics of the one or more features comprise: a localization of at least one of the one or more features.

6. The characterization system of claim 1, wherein the one or more characteristics of the one or more features comprise: one or more context attributes of at least one of the one or more features.

7. The characterization system of claim 1, wherein the one or more characteristics of the one or more features comprise: a classification scheme of the one or more features.

8. The characterization system of claim 1, wherein the one or more characteristics of the one or more features comprise: a size measurement of at least one of the one or more features.

9. The characterization system of claim 1, wherein the set of program instructions are further configured to cause the one or more processors to adjust a process tool based on the one or more characteristics of the one or more features.

10. The characterization system of claim 1, wherein the set of program instructions are further configured to cause the one or more processors to re-identify one or more defects based on the one or more enhanced images.

11. The characterization system of claim 1, wherein the set of program instructions are further configured to cause the one or more processors to identify one or more defects based on the one or more enhanced images.

12. The characterization system of claim 11, wherein the enhance the one or more sample specimen images and the identify the one or more defects occur in real-time.

13. The characterization system of claim 11, wherein the one or more sample specimen images are recorded and the identifying one or more defects occurs during at least one of a playback of the recorded one or more sample specimen images or offline reprocessing of data.

14. The characterization system of claim 1, wherein the one or more features are one or more defects, and wherein the set of program instructions are further configured to cause the one or more processors to re-detect at least one of the one or more defects based on the one or more characteristics of the one or more features.

15. The characterization system of claim 2, wherein the aligning the one or more training images with the one or more training design images comprises aligning the one or more training images with the one or more training design images to a sub-pixel accuracy.

16. The characterization system of claim 1, wherein the training design images comprise at least one of rendered training design images rendered from design data of one or more training specimens or derived training design images derived from the design data of the one or more training specimens.

17. The characterization system of claim 1, wherein the machine learning model comprises a deep learning predictive model.

18. The characterization system of claim 17, wherein the deep learning predictive model is a Generative Adversarial Network (GAN).

19. The characterization system of claim 1, wherein the one or more training images have a first resolution and the one or more training design images have a second resolution that is higher than the first resolution.

20. The characterization system of claim 19, wherein the one or more enhanced images have a third resolution that is higher than the first resolution.

21. The characterization system of claim 1, wherein the one or more training features are two or more training defects, each training defect of the two or more training defects being from a particular Design Based Group (DBG) of two or more different DBGs.

22. The characterization system of claim 2, wherein the generate the machine learning model is further based on at least one of rotated or flipped versions of both the one or more training images and the one or more training design images.

23. The characterization system of claim 1, wherein the one or more features include one or more polygon features, wherein the set of program instructions are further configured to cause the one or more processors to determine whether at least one of the one or more polygon features is a failed polygon feature that failed due to a hotspot.

24. A method for enhancing image quality comprising:

acquiring a machine learning model trained for correlating one or more training images and one or more training design images;

receiving one or more sample specimen images corresponding to one or more features of a sample specimen;

enhancing the one or more sample specimen images by generating one or more enhanced images with the machine learning model based on at least the one or more sample specimen images, wherein the one or more enhanced images have improved image quality relative to the one or more sample specimen images, the improved image quality comprising at least one of increased signal-to-noise ratio, increased resolution, or increased contrast; and determining, based on the one or more enhanced images, one or more characteristics of the one or more features, wherein the one or more characteristics of the one or more features comprise a defect classification type of at least one of the one or more features, wherein the defect classification type comprises one of a Defect of Interest (DOI) or a nuisance defect.

25. The method of claim 24, wherein the acquiring the machine learning model trained for correlating the one or more training images and the one or more training design images comprises:

acquiring the one or more training images comprising one or more training features of a one or more training specimens;

receiving the one or more training design images corresponding to the one or more training features of the one or more training specimens;

aligning the one or more training images with the one or more training design images corresponding to the one or more training features of the one or more training specimens;

generating the machine learning model based on the one or more training images and the one or more training design images.

26. The method of claim 24, wherein the acquiring the machine learning model trained for correlating the one or more training images and the one or more training design images comprises:

receiving the machine learning model, the machine learning model based on the one or more training images and the one or more training design images corresponding to and aligned with the one or more training images.

27. The method of claim 24, wherein the one or more characteristics of the one or more features comprise: a localization of at least one of the one or more features.

28. The method of claim 24, wherein the one or more characteristics of the one or more features comprise: one or more context attributes of at least one of the one or more features.

29. The method of claim 24, wherein the one or more characteristics of the one or more features comprise: a classification scheme of the one or more features.

30. The method of claim 24, wherein the one or more characteristics of the one or more features comprise: a size measurement of at least one of the one or more features.

31. The method of claim 24, further comprising adjusting a process tool based on the one or more characteristics of the one or more features.

32. The method of claim 24, further comprising re-identifying one or more defects based on the one or more enhanced images.

33. The method of claim 24, further comprising identifying one or more defects based on the one or more enhanced images.

34. The method of claim 33, wherein the enhancing the one or more sample specimen images and the identifying one or more defects occur in real-time.

35. The method of claim 33, wherein the one or more sample specimen images are recorded and the identifying one or more defects occurs during a playback of the recorded one or more sample specimen images.

36. The method of claim 24, wherein the one or more features are one or more defects, and wherein the method further comprises re-detecting at least one of the one or more defects based on the one or more characteristics of the one or more features.

37. The method of claim 25, wherein the aligning the one or more training images with the one or more training design images comprises aligning the one or more training images with the one or more training design images to a sub-pixel accuracy.

38. The method of claim 24, wherein the training design images comprises at least one of rendered training design images rendered from design data of one or more training specimens or derived training design images derived from the design data of the one or more training specimens.

39. The method of claim 24, wherein the machine learning model comprises a deep learning predictive model.

40. The method of claim 39, wherein the deep learning predictive model is a Generative Adversarial Network (GAN).

41. The method of claim 24, wherein the one or more training images have a first resolution and the one or more training design images have a second resolution that is higher than the first resolution.

42. The method of claim 41, wherein the one or more enhanced images have a third resolution that is higher than the first resolution.

43. The method of claim 24, wherein the one or more training features are two or more training defects, each training defect of the two or more training defects being from a particular Design Based Group (DBG) of two or more different DBGs.

44. The method of claim 25, wherein the generating a machine learning model is further based on at least one of rotated or flipped versions of both the one or more training images and the one or more training design images.

45. The method of claim 24, wherein the one or more features include one or more polygon features, wherein the method further comprises determining whether at least one of the one or more polygon features is a failed polygon feature that failed due to a hotspot.

*    *    *    *    *